(12) United States Patent
DeMarsh et al.

(10) Patent No.: US 6,436,971 B2
(45) Date of Patent: Aug. 20, 2002

(54) USE OF PDE 4-SPECIFIC INHIBITORS TO REDUCE THE SEVERITY OF A BACTERIAL INFECTION AFTER A RESPIRATORY VIRAL INFECTION

(75) Inventors: Peter L. DeMarsh, West Chester, PA (US); Susan B. Dillon, Alamo, CA (US); Gary Woodnutt, Chester Springs, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/779,401

(22) Filed: Feb. 8, 2001

Related U.S. Application Data
(60) Provisional application No. 60/181,385, filed on Feb. 9, 2000.

(51) Int. Cl.[7] ................................................ A01N 43/40
(52) U.S. Cl. ...................... 514/352; 514/285; 514/362; 514/363; 514/364; 514/381; 514/520; 514/521
(58) Field of Search ................................. 514/285, 520, 514/521, 362, 363, 364, 381

(56) References Cited

U.S. PATENT DOCUMENTS

| | | | | |
|---|---|---|---|---|
| 5,891,878 A | * | 4/1999 | Beasley et al. | 514/247 |
| 6,090,817 A | * | 7/2000 | Manley | 514/277 |

* cited by examiner

*Primary Examiner*—Dwayne C. Jones
*Assistant Examiner*—C. Delacroix-Muirheid
(74) *Attorney, Agent, or Firm*—James M. Kanagy; Charles M. Kinzig

(57) ABSTRACT

This invention relates to a method for the prophylaxis of or reducing the severity of post-viral bacterial infection by administering a PDE 4-specific inhibitor prior to or during the course of a viral infection or thereafter during the course of the bacterial infection.

10 Claims, 3 Drawing Sheets

The Effect of SB207499 Ariflo® in Influenza / Bacteria Co-Infection model

USE OF PDE 4-SPECIFIC INHIBITORS TO REDUCE THE SEVERITY OF A BACTERIAL INFECTION AFTER A RESPIRATORY VIRAL INFECTION

This application claims priority to provisional application 60/181,385, filed Feb. 9, 2000.

AREA OF THE INVENTION

This invention relates to a method for the prophylaxis of or reducing the severity of post respiratory viral infection in the respiratory tract by bacteria by administering a PDE 4-specific inhibitor prior to or during the course of a viral infection or thereafter during the course of the bacterial infection.

BACKGROUND

Primary respiratory tract viral infections have been shown to lead to increased susceptibility to secondary bacterial infections [Loosli C. G. 1973, Med. 52, 369–384; Stuart-Harris C. H., Laird J., Tyrell D. A., Kelsall M. H., Franks Z. C., Pownall M. 1949, J. Hyg. 47; 434; and Stuart-Harris C. H. 1966, Brit. Med. J. 149; 217]. The mechanisms of this susceptibility are poorly understood. And there is no prophylactics or treatments available for reducing or moderating this susceptibility. Herein there is provided a model for studying this phenomenon and a demonstrated method for reducing this susceptibility by administering a PDE 4 specific inhibitor.

Streptococcus pneumoniae is regarded as one of the most common causes of community-acquired pneumonia and is an important cause of illness and death in industrialized countries. S. pneumoniae colonizes the human nasophararynx and in some circumstances the organisms spread to cause upper or lower respiratory tract infection. The mechanisms underlying the transition from a benign colonization to disease are not well understood. A number of mechanisms have been proposed but the nature of this transition remains to be discovered.

Epidemiological studies have demonstrated that viral infections pre-dispose the host lung to bacterial pneumonia and secondary bacterial pneumonia is the most frequent complication of influenza infection in man [Loosli C. G. 1973, Med. 52, 369–384; Stuart-Harris C. H., Laird J., Tyrell D. A., Kelsall M. H., Franks Z. C., Pownall M. 1949, J. Hyg. 47; 434; and Stuart-Harris C. H. 1966, Brit. Med. J. 149; 217]. Investigators have demonstrated in vitro that cells stimulated with either cytokines or virus show enhanced bacterial adherence and that bacterial adherence to host tissues is an essential step in bacterial colonization and infections [Jones W. T., Menna J. H. 1982, Infect. Immun. 38; 791–794; Jiang Z., Nagata N., Molina E., Bakaletz L. O., Hawkins H., Patel J. A. 1999, Infect. Immun. 67; 187–192; Sanford B. A., Shelokov A., Ramsay M. A. 1978, J. Infect. Dis. 137; 176–181; Geelen S., Bhattacharyya C., Tuomanen E. 1993, Infect. Immun. 61; 1538–1543; and Hakansson A., Kidd A., Wadell G., Sabharwal H., Svanborg C. 1994, Infect. Immun. 62, 2707–2714.]

Phase variation of pneumococci has been demonstrated to be one of the virulence mechanisms of respiratory tract infections. For S. pneumoniae the transparent phenotype has been shown to adhere to lung epithelial cells and to be more virulent in an infant rat colonization model than the opaque phenotype [Kim J. O., Weiser J. N. 1998, J. Infect. Dis. 177:368–377; and Weiser J. N., Austrian R., Sreenivasan P. K., Masure H. R. 1994, Infect. Immun. 62; 2582–2589]. The mechanism of the altered virulence of S. pneumoniae phenotypes has been shown to be linked to the cell wall and the production of the capsular glycoprotein CbpA [Berube L. R., et al, 1999, Micro. Path. 26; 65–75 and Geelen S. et al, 1993, Infect. Immun., 61; 1538–1543].

Here-in there is described a murine model of sub-lethal influenza infection followed by Streptococcus pneumoniae co-infection. Also disclosed is the finding that administrating a PDE 4-specific inhibitor reduces the susceptibility of a mammal to post-viral bacterial infection.

SUMMARY OF THE INVENTION

This invention relates to a means for reducing the severity of or preventing a bacterial infection of the respiratiory tract following a respiratory viral tract infection by administering an effective amount of a PDE 4-specific inhibitor alone or in combination with a pharmaceutically acceptable excipient prior to or during the course of the viral infection, during the course of both the viral infection and the bacterial infection following thereafter, or during the course of the bacterial infection alone.

SPECIFIC EMBODIMENTS

Figure 1:
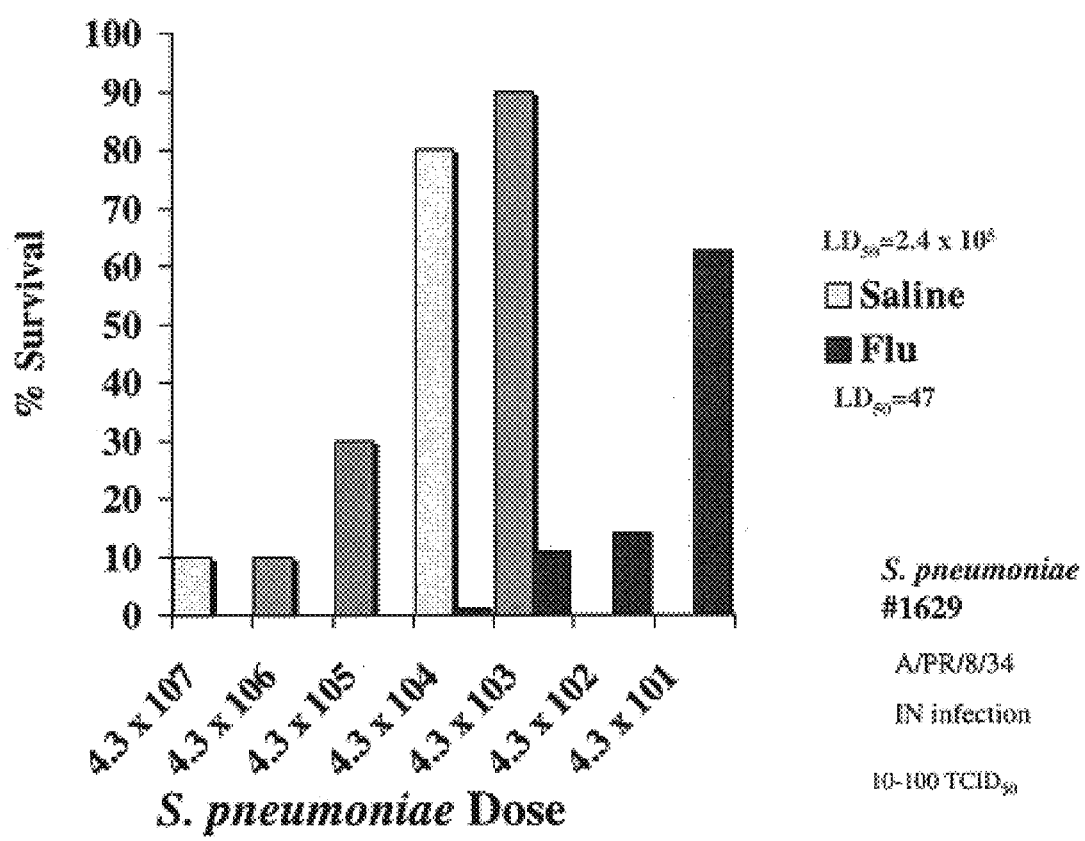
FIG. 1 is a graph of the S. pneumoniae $LD_{50}$ determination in non-infected vs. sub-lethally influenza infected mice.
Figure 2:
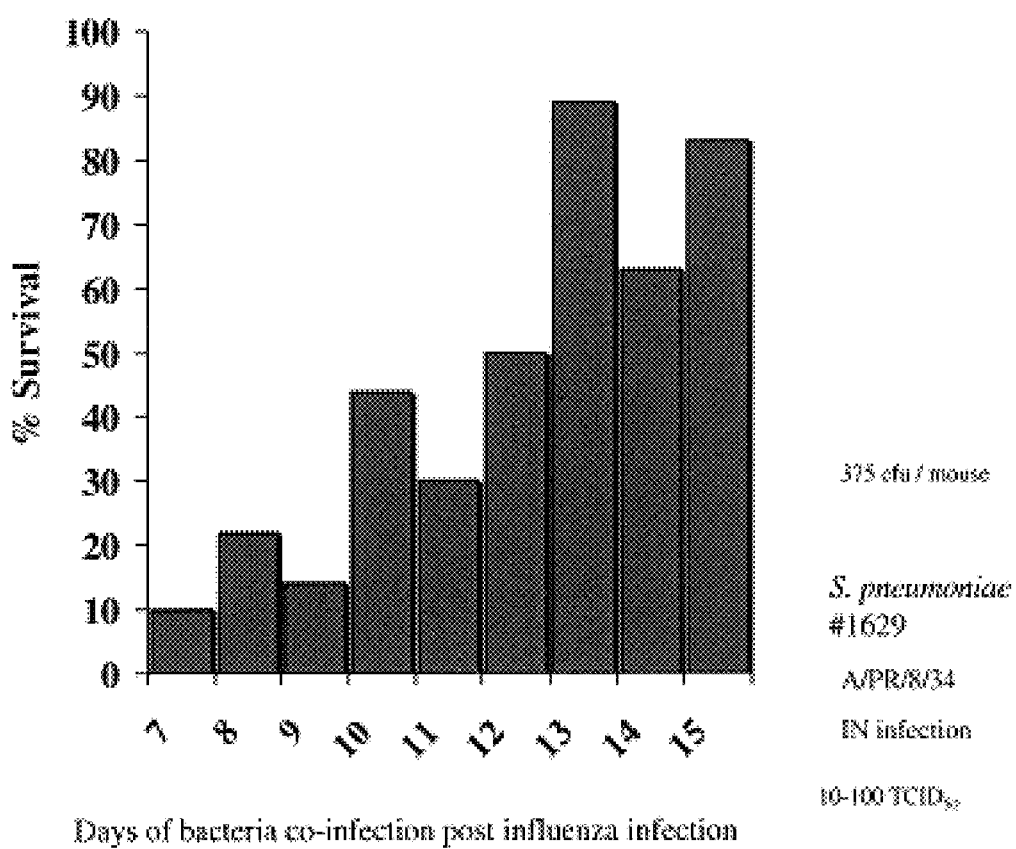
FIG. 2 is a chart of the survival following S. pneumoniae challenge following treatment with a PDE 4 inhibitor.

Respiratory viral infections and course of treatment

This invention can be used in those situations where a respiratory viral infection is or will most likely occur. It can be used regardless of the type of viral material causing the respiratory infection and regardless of the locus of the infection, be it in the upper respiratory tract or the lower tract or both. Numerous viruses are known to be involved in respiratory viral infections, including but not limited to Rhinovirus, Influenza, Respiratory Syncytial Virus, Parainfluenza, Adenovirus, Enterovirus and Coronavirus.

The PDE4 inhibitor is administered in several ways: i) during the course of the respiratory viral infection, starting at any time and running for less that the full length of the viral infection; ii) during the whole of the course of the respiratory viral infection or some part thereof, and during the whole of the course of the bacterial infection, or some part thereof; or iii) at the start of or during the course of the bacterial infection or some part thereof. In addition, the inhibitor can be administered prior to the onset of a respiratory viral infection, and preferably continued for some period during the course of the infection. Furthermore, an inhibitor can be administered intermitently during the respiratory viral infection phase, or over the course of both the viral infection and the subsequent bacterial infection.

PDE 4 Inhibitors

The inhibitors of interest in this invention are PDE 4 inhibitors. Of particular interest are those which are specific for PDE 4. A preferred group of inhibitors are those that have an $IC_{50}$ ratio (high/low binding) of about 0.1 or greater as further described in U.S. Pat. No. 5,998,428; this patent is incorporated herein in full by reference as if fully set forth herein. A preferred standard for PDE 4-specific inhibitors which can be used in this invention is one where the compound has an $IC_{50}$ ratio of about 0.1 or greater; said ratio being the ratio of the $IC_{50}$ value for competing with the binding of 1 nM of $[^3H]R$-rolipram to a form of PDE 4 which binds rolipram with a high affinity over the $IC_{50}$ value for inhibiting the PDE 4 catalytic activity of a form which binds rolipram with a low affinity using 1 $\mu M[^3H]$-cAMP as the substrate.

Other PDE 4 inhibitors that may be included in these formulations include those set out in U.S. Pat. No. 5,552,438 issued Sep. 3, 1996. This patent and the compounds it discloses are incorporated herein in full by reference. The compound of particular interest, which is disclosed in U.S. Pat. No. 5,552,438, is cis-4-cyano-4-[3-(cyclopentyloxy)-4-methoxyphenyl]cyclohexane-1-carboxylic acid (Ariflo®) and its salts, esters, pro-drugs or physical forms. Other PDE 4 inhibitors which may be of interest include: AWD-12-281 from Astra (Hofgen, N. et al. 15th EFMC Int Symp Med Chem (Sept 6–10, Edinburgh) 1998, Abst P.98); a 9-benzyladenine derivative nominated NCS-613 (INSERM); D-4418 from Chiroscience and Schering-Plough; a benzodiazepine PDE 4 inhibitor identified as CI-1018 (PD-168787; Parke-Davis/Warner-Lambert); a benzodioxole derivative Kyowa Hakko disclosed in WO 9916766; V-1 1294A from Napp (Landells, L. J. et al. Eur Resp J [Annu Cong Eur Resp Soc (Sept 19–23, Geneva) 1998] 1998, 12(Suppl. 28): Abst P2393); roflumilast (CAS reference No 162401-32-3) and a pthalazinone (WO 9947505) from Byk-Gulden; and a compound identified as T-440 (Tanabe Seiyaku; Fujii, K. et al. *J Pharmacol* Exp Ther, 1998, 284(1): 162). Preferred compounds of this invention are those which have an $IC_{50}$ ratio of greater than 0.5, and particularly those compounds having a ratio of greater than 1.0. The most preferred compounds are roflumilast and cis-4-cyano-4-[3-(cyclopentyloxy)-4-methoxyphenyl]cyclohexane-1-carboxylic acid.

In addition, one or more of these PDE 4 inhibitors can be combined with other methods for treating influenza and/or bacterial infections. For example, a PDE 4 inhibitor could be co-administered with a treatment for influenza during the course of the viral infection. Examples of such drugs are alpha and beta interferon, Inosine pranobex, moroxydine hydrochloride, zanamivir, rimantadine, rimantadine hydrochloride, oseltamivir phosphate and the like.

If the PDE 4 inhibitor is administered during the course of the bacterial infection, an anti-infective agent may be co-administered at the same time or in conjunction with the PDE 4 inhibitor.

As regards antibiotics, they are a very diverse class of compounds which often classified and discussed in groups. Herein those of greatest interest will be the drugs and preparations which treat infections in the lung. *S. pneumoniae* is often found in patients with pneumonia. It is sensitive to the penicillins, benzylpenicillin, amoxycillin, or ampicillin; to cephalosporins; to erythromycin; or to co-trimoxazole. *Mycoplasma pneumoniae* is also an important cause of community-acquired pneumonia. Erythromycin or tetracycline are the antibacterials of choice against *M. pneumoniae;* erythromycin is usually recommended when mycoplasmal pneumonia is suspected. Bacteria that may be responsible for community-acquired pneumonia include *Haemophilus influenzae* and, more recently, *Moraxella (Branhamella) catarrhalis* especially in patients with chronic lung disease; *Legionella pneumophila* (see Legionnaires' Disease); *Chlamydia psittaci* (see Psittacosis); *Chlamydia pneumoniae* (formerly known as the TWAR strain of *Chlamydia psittaci*); and *Coxiella burnetii* (see Q fever). A fuller discussion of pulmonary infections and antibiotics for their treatment can be found in the likes of Tomes CPS™ System from Micromedex. This publication is available on the Web courtesy of Micromedex, Inc., The section relating to antibiotics relevant to this invention has the URL
http://www.tomescps.com/DKS/DATAJMT/MTM1-z.htm#1 -a5-328-k.

For the purposes of this invention, it is preferred to administer the PDE 4 inhibitorin an amount between about 1 mg to 200 mg, more preferably 5 to 100 mg, and most preferably between 5, or 10 to 60 mg of the active ingredient. Additional preferred dosage amounts are about within these ranges are 10, 15, 20, 30, 40, 50, 60, 70, 80 or 90 mg per preparation. The inhibitor can be administered by any route. A perfered formulation will be an oral immediate release tablet or a oral controlled release tablet. The inhibitor may be administered up to 6 times per day, though a twice or once a day dosing regime is preferred.

Assay

The assay used here-in is a murine model where the subject is administered a sub-lethal influenza infection followed by *Streptococcus pneumoniae* co-infection and then evaluated for survival. In this model, mice are infected with a dose of influenza virus that leads to a non-lethal self-limiting infection. Mice that had recently cleared an influenza infection required 4 $\log_{10}$ fewer *S. pneumoniae* to cause mortality than normal non-influenza challenged animals. While mice dosed with saline required $10^4$ cfu of *S. pneumoniae* to show significant mortality, influenza challenged animals showed significant mortality with as few as 280-cfu pneumococci.

Mice: Male CBA/J mice obtained from Jackson Laboratories (Bar Harbor, Me.) 3 to 4 weeks of age were utilized. Mice were housed 10 per cage in standard laboratory plastic caging and fed lab chow and water ab libitum. All animal procedures were performed in accordance with the highest standards for the humane handling, care and treatment of research animals.

Preparation 1

Bacteria: Two separate *S. pneumoniae* clinical isolates (strains #1629 and #0100993) were individually animal-passaged in mice and subsequently recovered and plated onto sheep red blood cell trypticase soy agar (TSA) then stored frozen at −70° C. The re-isolated organisms were grown overnight on chocolate TSA (Becton Dickinson, Md.) and harvested in saline. The concentration of the stock was determined by absorbance (560 nm) using a spectrophotometer (Beckman DU 640B, Calif.). Inoculum doses were based on viable counts determined by scoring colony-forming units on sheep reb blood TSA.

Preparation 2

Virus: Influenza type A virus strain A/PR/8/34 sub type H1N1 (American Type Culture Collection, Rockville, Md.) was propagated in the allantoic cavity of 10 day old fertilized chicken eggs. The eggs were incubated for 48 hrs at 37° C., refrigerated for 2 ½ hours at 4° C. then the allantoic fluid was harvested. Pooled allantoic fluid was centrifuged (1,000 rcf; 15 min; 4° C.) to remove cells, and then divided into aliquots for storage at −70° C. The titer of the stock culture of virus was $1.0 \times 10^9$ $TCID_{50}$/ml.

Preparation 3

Mice were anesthetized with ketamine/xylazine (40 mg/kg;10 mg/kg) and inoculated intranasally (IN) with 50 $\mu$l of influenza virus or vehicle control. Mice that were co-infected with bacteria were anesthetized as above then infected IN with 25 $\mu$l of bacterial suspension.

Preparation 4

Virus Titrations: Lungs were removed aseptically and placed in vials containing 1 micron glass beads (Biospec Products, Bartlesville, Okla.) and 1 ml. of Eagles minimal essential medium with penicillin and streptomycin. The lungs were homogenized for 45 seconds using a mini-bead beater (Biospec Products, Bartlesville, Okla.); the vials were then centrifuged at 1,000 rcf for 15 minutes at 4° C., and the lung supernatants were frozen at −20° C. Virus was quantitated in an in vitro microassay using Madin-Darby canine kidney (MDCK) cells (r). Serial dilutions of lung homogenates (in medium plus 2.5 ug/ml trypsin) were added to round-bottom microtiter wells containing adherent MDCK cells. After 5 days of incubation at 37° C. (5% $CO_2$), 50 $\mu$l of 0.5% chick red blood cells were added per well, and agglutination was read after 1 hour at room temperature. The virus titer is expressed as 50% tissue culture infective dose ($TCID_{50}$) calculated by logistic regression (s).

Preparation 5

Bacterial Titrations: Lungs were harvested as above and homogenized (Stomacher 80 Seward Medical, London, England) in 1.0 ml of saline. Serial dilutions were made in saline and inoculated onto sheep red blood cell TSA for enumeration.

Preparation 6

Histochemistry: Whole lungs were inflated-fixed with 10% formalin in phosphate-buffered saline and immersed in fixative for 24 hrs at 4° C. Tissues were processed for paraffin sectioning using an automated tissue processor. Paraffin-embedded lungs were serially sectioned at 6 $\mu$m and prepared for hemotoxylin and eosin (H&E) staining.

Preparation 7

Cytokine analysis: Bronchiolar alveolar lavage fluid (BALF) cytokine levels were measured by quantitative ELISA using commercially available kits. Mice were sacrificed and the trachea exposed, a cannula was inserted and ligated. By syringe each lung was flushed three times with 1 ml of normal saline. The BALF was centrifuged at 2000 rcf for 1 min. and the supernatant was stored at −70° C. The cytokine concentrations and thresholds were determined as described by the manufacturer; TNF-$\alpha$, IL-6, IFN-$\gamma$, and KC (R&D Systems, Minneapolis, Minn.) IL-10, IL-1$\beta$ (Biosource International, Camarillo, Calif.).

Preparation 8

Determination of pulmonary functions: Barometric plethysmography was conducted on unrestrained mice using whole body plethysmography (Buxco, Troy, N.Y.), as described (Hamelmann et al, 1997, Noninvasive measurement of airway responsiveness in allergic mice using barometric plethysmography, Amer. J. of Resp. Crit. Care Med. 156, 766–775.). Briefly, individual chambers were calibrated prior to each reading, mice were placed in the main chamber, and pressure differences between the main chamber and a reference chamber were recorded for 2 minutes. Using the Biosystem Pulmonary Analyzer software (Buxco) the resultant box pressure was used to calculate the phases of the respiratory cycle, tidal volumes, and enhanced pause (Penh). Penh value is a function of the proportion of maximal expiratory to maximal inspiratory box pressure signals and the timing of expiration. Uninfected or Influenza A/PR/8/34 infected mice dosed with Ariflo® at 10 or 30 mg/Kg/day (days 0–8) were evaluated daily for 16 days.

EXAMPLE 1

Sub-lethal Influenza Infection Model.

Initial 21-day survival studies determined that mice challenged intranasally (IN) with as few as 350 $TCID_{50}$ of influenza strain A/PR/8134 resulted in 80% to 90% of the mice succumbing to the infection. Lower doses of virus resulted in over 95% of the animals surviving. From these studies a dose range of 10 to 50 $TCID_{50}$ was selected as a sub-lethal dose for use in co-infection models. To confirm that mice challenged with this low inocula have a self-limiting infection, mice were challenged IN with 10 to 50 $TCID_{50}$ and sacrificed 2 hrs after infection, on days 1 to 11 and day 14. The lungs were harvested and the viral titers determined. Two hours after infection there was no virus detectable from the lungs of the mice. However, by day 1 after infection there was detectable virus in the lung homogenates. The virus titers peaked on day 5 with $4.8 \times 10^5$ $TCID_{50}$ in the lungs. The virus titers decreased after day 5 with all the animals being clear of virus by day 9 after infection.

Histopathology from these animals show a progressive lower respiratory tract infection with heavy thickening of the alveoli by day 6 after infection. There is interstitial pneumonitis with capillary thrombosis and necrosis of the of the alveolar walls. Both alveolar type I and II cells lining the alveolar spaces slough. While the virus was reduced to undetectable levels by day 9 after infection, considerable consolidation of the lungs remains. By day 15 after infection, although some consolidated areas remain, there are increased areas of improved lung.

Acute Influenza A infection results in a reduction in pulmonary functions. Whole body plethysmography is currently accepted as a measurement for pulmonary resistance in allergic or infected mice (Haczku et al. 1997; Hamelmann et al. 1997a; Hamelmann et al. 1997b; Schwarze et al. 1998; van Schaik et al. 1998). Penh was used in this study as a parameter representing pulmonary functions. Uninfected or Influenza A/PR/8/34 infected mice were evaluated daily for 16 days. Penh values were elevated above baseline (0.4–0.5) in all animals between days 5–16 post infection.

The wet and dry lung weights from sub-lethal influenza challenged mice were evaluated as follows: The wet and dry lung wts were evaluated from mice sub-lethally challenged with influenza virus; n=4 per group. The wet lungs weights, indicated an increasing pneumonitis with significant increases in wet weight as early as day 2 after infection followed by a rapid increase over days 5 and 6. The dry lung weights did not reach statistically significant increases in weight until day 6 after infection. Otherwise the dry lung wts reflected the wet lung weights. The wet lung weights showed small but statistically significant increases as early as day 2 with larger increases on days 5 to 6. The dry lung weights did not show significant increases until day 6 after infection. Both the wet and dry weights remained elevated after the virus cleared, day 9.

The cytokine response to influenza challenge was evaluated in bronchiolar lavage fluid (BALF), increases were seen in IL-6, IFN$\gamma$, and the chemokine KC (Table 1). All showed peak levels on day 8 after challenge with levels decreasing to pre-infection levels by day 10. TNF$\alpha$, IL-10, IL-1$\beta$, and IL-2 were also evaluated, however no significant elevation in levels ware found for these cytokines at any time point.

TABLE 1

Cytokine Concentration (pg/ml) in the BALF from Sub-lethally Infected Mice

|  | Day 1 | Day 3 | Day 6 | Day 8 | Day 10 | Day 13 | Day 15 |
|---|---|---|---|---|---|---|---|
| IL-6 | 120 ± 15 | 118 ± 12 | 448 ± 221 | 575 ± 170* | 279 ± 194 | 116 ± 6 | 128 ± 10 |
| IFN-γ | 34 ± 10 | 33 ± 16 | 692 ± 328* | 2392 ± 783* | 87 ± 49 | 30 ± 5 | 30 ± 2 |
| KC | 16 ± 2 | 24 ± 7 | 112 ± 38* | 206 ± 52* | 73 ± 42 | 42 ± 11 | 23 ± 13 |
| TNF-α | 40 ± 21 | 16 ± 10 | 19 ± 2 | 33 ± 15 | 16 ± 5 | 13 ± 1 | 22 ± 13 |
| IL-10 | 272 ± 59 | 177 ± 96 | 255 ± 86 | 242 ± 117 | 148 ± 35 | 107 ± 49 | 208 ± 112 |
| IL-1β | 84 ± 29 | 203 ± 90 | 130 ± 19 | 128 ± 89 | 99 ± 79 | 61 ± 58 | 105 ± 41 |
| IL-2 | 2 ± 1 | 2 ± 1 | 2 ± 1 | 2 ± 1 | 2 ± 1 | 2 ± 1 | 1 ± 1 |

* $P < 0.05$

EXAMPLE 2
Establishment of Bacterial Co-Infection Model

In initial studies mice were infected IN with a sub-lethal dose of influenza virus or non-virally infected vehicle controls. On day 9 after infection the mice were given a second challenge IN with S. pneumoniae (strain #0100993). The non-virally infected mice were resistant to infection requiring $2.8 \times 10^7$ cfu/mouse S. pneumoniae to lead to no animals surviving. The calculated $LD_{50}$ for non-virally infected mice challenged with S. pneumoniae was $4.7 \times 10^5$ cfu/mouse. In contrast, the mice challenged with a sub-lethal dose of influenza were sensitive to a second challenge with S. pneumoniae with all the mice co-infected with $2.8 \times 10^2$ cfu/mouse of S. pneumoniae dying. The $LD_{50}$ for the virus infected mice was only 66 cfu/mouse. These results replicated with a second strain of S. pneumoniae (strain # 1629), the non-virus infected animals showed a S. pneumoniae $LD_{50}$ of $2.4 \times 10^5$ cfu/mouse while the virus challenged animals showed an $LD_{50}$ of only 47 cfu/mouse.

Initial studies in the bacterial co-infection model were performed on day 9 after virus challenge because that was the first day the animals were influenza virus culture negative. A study was done to determine the length of time that the increased sensitivity to infection with S. pneumoniae was sustained. In this study mice were challenged with influenza as above and then separate groups were challenged with 375 cfu of S. pneumoniae on day 7 through 15 (FIG. 1). Mice were challenged with a sub-lethal dose of influenza virus; n=10 per group. On days 7 to 15 after infection individual groups of mice were challenged with 375 cfu/mouse of S. pneumoniae. The mice challenged with pneumococci just before of just after the virus is cleared, days 7 to 9, showed high susceptibility to the secondary infection. The mice challenged with pneumococci at latter time points, day 10 to 15, showed increasing resistance to infection. The animals did not return to normal levels of pneumococcal resistance at any time point tested up to 15 days. The mice co-infected with bacteria on days 7 to 9 all had a low survival rate. Mice co-infected on later days showed improved survival, although this improvement did not make the virus challenged animals as resistant to infection as normal saline challenged animals.

To determine if the decrease in survival demonstrated in co-infected mice was due to bacterial pneumonia, mice were infected with virus as above and challenged on day 9 with S. pneumoniae (strain # 0100993) 492 cfu/mouse. Mice were sacrificed at 2, 24 and 48 hrs post bacterial challenge and whole lungs were homogenized and the number of S. pneumoniae determined for each animal. Two hrs after infection there were few recoverable organisms from the lungs of the mice. However, by 24 hrs post infection the number of recovered S. pneumoniae were $8.9 \times 10^5$ cfu/mouse, at 48 hrs the numbers had climbed to $2.1 \times 10^6$ cfu/mouse. Later time points could not be taken since the animals start to succumb to the infection on day 3 after infection with all the animals dying by day 5. These results replicated with a second strain of S. pneumoniae (strain # 1629), with $3.8 \times 10^5$ cfu/mouse being recovered from the lungs at 24 hrs after infection climbing to $1.6 \times 10^8$ cfu/mouse at 48 hrs post bacterial challenge.

EXAMPLE 3
Pretreatment With a PDE 4 Inhibitor

Figure 3:
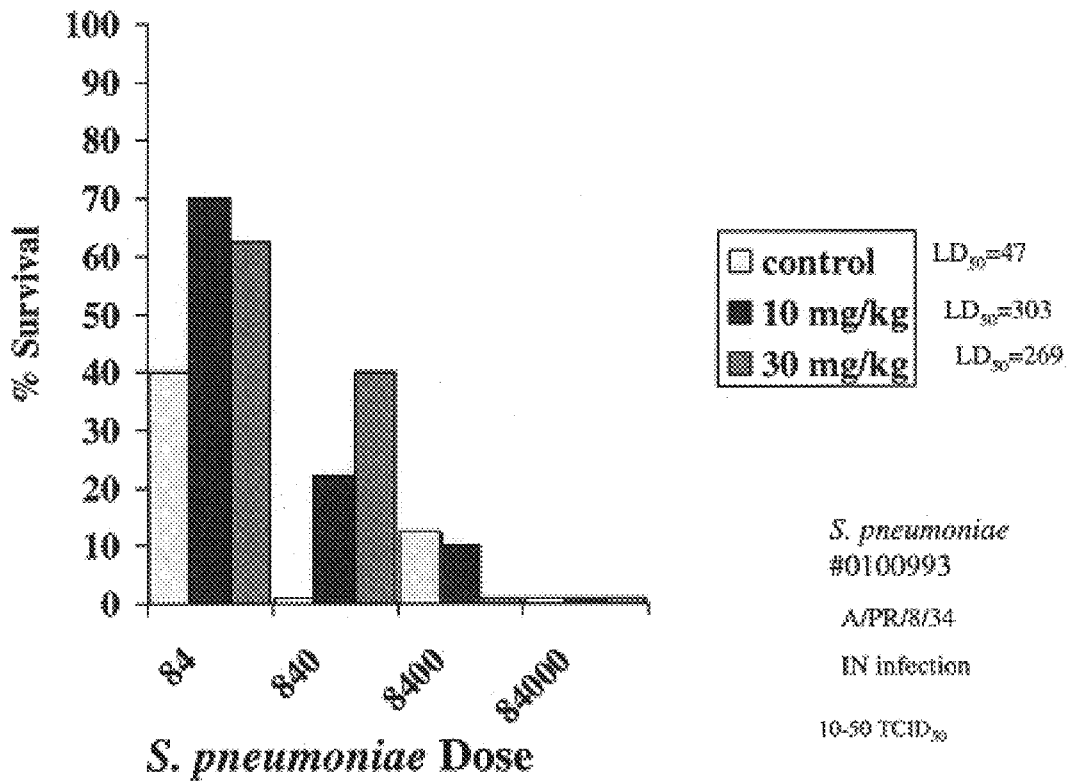
FIG. 3 is a chart of the colony-forming-units/mouse following a S. pneumoniae challenge following treatment with a PDE 4 inhibitor.

In this study the mice were treated orally with 10 or 30 mg/kg of cis-4-cyano-4-[3-(cyclopentyloxy)-4-methoxyphenyl]cyclohexane-1-carboxylic acid once daily on days 0 to 9. The vehicle was 2% methylcellulose. These mice were infected with a sub-lethal dose of influenza virus IN as described above. On day 9 after influenza infection the mice were challenged IN with S. pneumoniae (strain #0100993) prepared as described above. The mice were then followed for survival. The mice treated with control diluent had an $LD_{50}$ of 72 and Ariflo (10, 30 mg/kg) treated mice had a $LD_{50}$ of 252 and 221 cfu/mouse respectively of S. pneumoniae. See FIG. 3 for survival rates.

What is claimed is:

1. A method for reducing the severity of or preventing a bacterial infection of the respiratory tract following a respiratory viral tract infection by administering an effective amount of a PDE 4-specific inhibitor alone or in combination with a pharmaceutically acceptable excipient prior to or during the course of the viral infection, during the course of both the viral infection and the bacterial infection following thereafter, or during the course of the bacterial infection alone.

2. The method of claim 1 wherein the PDE 4 inhibitor is administered during the course of the viral infection.

3. The method of claim 1 wherein the PDE 4 inhibitor is administered during the course of the viral infection and during the course of the bacterial infection.

4. The method of claim 1 wherein the PDE 4 inhibitor is administered during the course of the bacterial infection.

5. The method of claim 3 wherein an antibiotic is administered during the course of the bacterial infection.

6. The method of claim 4 wherein an antibiotic is administered during the course of the bacterial infection.

7. The method of claim 3 wherein, in addition to the PDE4 inhibitor, an antiviral is administered during the course of the viral infection.

8. The method of claim 4 wherein, in addition to the PDE4 inhibitor, an antiviral is administered during the course of the viral infection.

9. The method of claim 1 wherein the inhibitor is administered orally as a controlled-release tablet.

10. The method of claim 1 wherein the inhibitor is administered intranasally or by aerosol to the respiratory tract.

* * * * *